(12) United States Patent
Gill et al.

(10) Patent No.: US 9,452,241 B2
(45) Date of Patent: Sep. 27, 2016

(54) NEUROSURGICAL INSTRUMENTS

(75) Inventors: Stephen Streatfield Gill, Bristol (GB); Mathew David Frederick Stratton, Stroud (GB); Hugo George Derrick, Bristol (GB)

(73) Assignee: RENISHAW (IRELAND) LIMITED, Swords (IE)

( * ) Notice: Subject to any disclaimer, the term of this patent is extended or adjusted under 35 U.S.C. 154(b) by 0 days.

(21) Appl. No.: 12/310,210

(22) PCT Filed: Aug. 20, 2007

(86) PCT No.: PCT/GB2007/003178
§ 371 (c)(1),
(2), (4) Date: Feb. 17, 2009

(87) PCT Pub. No.: WO2008/020241
PCT Pub. Date: Feb. 21, 2008

(65) Prior Publication Data
US 2009/0198218 A1    Aug. 6, 2009

(30) Foreign Application Priority Data
Aug. 18, 2006 (GB) .................................. 0616411.5

(51) Int. Cl.
*A61M 25/00* (2006.01)
*A61M 25/06* (2006.01)
(Continued)

(52) U.S. Cl.
CPC .............. *A61L 31/028* (2013.01); *A61M 25/00* (2013.01); *A61M 25/005* (2013.01);
(Continued)

(58) Field of Classification Search
CPC ................ A61M 25/0045; A61M 2210/0693; A61M 25/00; A61M 2025/0046; A61M 2025/0047; A61M 2025/0048; A61M 2025/0681; A61M 2025/09091; A61M 2210/0687; A61M 25/005; A61M 25/0053; A61M 2025/0042; A61L 31/028
USPC .............. 604/158, 164.09, 164.11, 181, 264, 604/524, 103
See application file for complete search history.

(56) References Cited

U.S. PATENT DOCUMENTS 4,230,123 A    10/1980 Hawkins, Jr.
4,613,324 A *  9/1986 Ghajar .......................... 604/539
(Continued)

FOREIGN PATENT DOCUMENTS

CN    1672649 A    9/2005
EP    0 266 091 A2  5/1988
(Continued)

OTHER PUBLICATIONS

Morrison et al.; "Focal delivery during direct infusion to brain: role of flow rate, catheter diameter, and tissue mechanics;" *The Journal of American Regulatory, Integrative and Comparative Physiology*; Oct. 1999; pp. 1218-1229; vol. 277—Issue No. 4; Bethesda, Maryland, USA.
(Continued)

*Primary Examiner* — Emily Schmidt
*Assistant Examiner* — Lauren M Peng
(74) *Attorney, Agent, or Firm* — Oliff PLC

(57) ABSTRACT

A catheter assembly for insertion into the brain. The assembly comprises a first length of tubing made of a first material. A second material surrounds the first length of tubing, the second material being more flexible than the first material and having a hardness of less than 50 Rockwell E. The second material provides damping to the first length of tubing.

29 Claims, 3 Drawing Sheets

(51) Int. Cl.
*A61M 25/09* (2006.01)
*A61L 31/02* (2006.01)

(52) U.S. Cl.
CPC ..... *A61M 25/0045* (2013.01); *A61M 25/0053* (2013.01); *A61M 2025/0042* (2013.01); *A61M 2025/0046* (2013.01); *A61M 2025/0047* (2013.01); *A61M 2025/0048* (2013.01); *A61M 2025/0681* (2013.01); *A61M 2025/09091* (2013.01); *A61M 2210/0687* (2013.01); *A61M 2210/0693* (2013.01)

(56) References Cited

U.S. PATENT DOCUMENTS

| | | | |
|---|---|---|---|
| 4,659,329 | A | 4/1987 | Annis |
| 4,850,974 | A | 7/1989 | Bickelhaupt et al. |
| 5,207,648 | A * | 5/1993 | Gross ............... A61M 25/0014 604/164.09 |
| 5,312,356 | A * | 5/1994 | Engelson et al. ......... 604/164.13 |
| 5,437,644 | A * | 8/1995 | Nobles ..................... 604/164.11 |
| 5,759,173 | A | 6/1998 | Preissman et al. |
| 5,797,858 | A | 8/1998 | Rourke |
| 5,891,100 | A | 4/1999 | Fleckenstein |
| 6,030,369 | A * | 2/2000 | Engelson et al. ............. 604/264 |
| 6,080,134 | A | 6/2000 | Lotti et al. |
| 6,086,008 | A | 7/2000 | Gray et al. |
| 6,203,526 | B1 | 3/2001 | McBeth et al. |
| 6,203,537 | B1 * | 3/2001 | Adrian .............................. 606/1 |
| 6,217,557 | B1 * | 4/2001 | H.ang.kansson et al. ......... 604/167.06 |
| 6,582,400 | B1 | 6/2003 | Hawk et al. |
| 6,609,020 | B2 | 8/2003 | Gill |
| 6,652,548 | B2 * | 11/2003 | Evans et al. .................. 606/159 |
| 6,926,711 | B2 * | 8/2005 | Lentz et al. ..................... 606/21 |
| 2003/0055447 | A1 | 3/2003 | Lee et al. |
| 2003/0093011 | A1 | 5/2003 | Jalisi |
| 2003/0109823 | A1 | 6/2003 | Hobot et al. |
| 2004/0073154 | A1 * | 4/2004 | Borgesen .......................... 604/8 |
| 2004/0215162 | A1 * | 10/2004 | Putz ....................... A61B 5/031 604/500 |
| 2005/0004554 | A1 | 1/2005 | Osborne |
| 2005/0061329 | A1 * | 3/2005 | Tran et al. .................... 128/831 |
| 2005/0154297 | A1 | 7/2005 | Gill |
| 2006/0025752 | A1 * | 2/2006 | Broaddus et al. ............. 604/537 |
| 2006/0129126 | A1 * | 6/2006 | Kaplitt et al. ................ 604/513 |
| 2006/0135945 | A1 * | 6/2006 | Bankiewicz et al. ......... 604/506 |
| 2007/0016100 | A1 | 1/2007 | Miller |
| 2007/0276340 | A1 | 11/2007 | Poston et al. |
| 2009/0088695 | A1 | 4/2009 | Kapur et al. |
| 2009/0143764 | A1 | 6/2009 | Nelson |
| 2011/0282319 | A1 | 11/2011 | Gill |
| 2013/0158578 | A1 | 6/2013 | Ghodke et al. |
| 2014/0171760 | A1 | 6/2014 | Singh et al. |
| 2014/0171902 | A1 | 6/2014 | Singh et al. |

FOREIGN PATENT DOCUMENTS

| | | |
|---|---|---|
| EP | 0 643 979 A1 | 3/1995 |
| EP | 0 597 341 B1 | 1/1997 |
| EP | 1155708 A2 | 11/2001 |
| EP | 1155708 A3 | 11/2001 |
| EP | 2258437 A1 | 12/2010 |
| FR | 2 530 958 A1 | 2/1984 |
| GB | 1 530 324 | 10/1978 |
| GB | 2 008 411 A | 6/1979 |
| GB | 2 132 898 A | 7/1984 |
| GB | 2 330 078 A | 4/1999 |
| GB | 2 355 665 A | 5/2001 |
| JP | A-2005-323658 | 11/2005 |
| WO | WO 99/34855 A1 | 7/1999 |
| WO | WO 99/55408 A1 | 11/1999 |
| WO | WO 03/077764 A1 | 9/2003 |
| WO | WO 03/077784 A1 | 9/2003 |
| WO | WO 03/077785 A1 | 9/2003 |
| WO | WO 2005/035043 A2 | 4/2005 |
| WO | 2007/024841 A2 | 3/2007 |
| WO | 2007/024841 A3 | 3/2007 |
| WO | 2007/133776 | 11/2007 |
| WO | 2008/020241 | 2/2008 |
| WO | 2009/101397 | 8/2009 |
| WO | 2012/031275 A2 | 3/2012 |
| WO | 2012/031275 A3 | 3/2012 |

OTHER PUBLICATIONS

Raghavan et al.; "Convection-enhanced delivery of therapeutics for brain disease, and its optimization;" *Neurosurgical Focus*; Apr. 2006; pp. 1-13; vol. 20—Issue No. 3.

Apr. 12, 2013 Search Report issued in European Patent Application No. EP 13 00 1067.

Bankiewicz, Krys S. et al. "Convection-Enhanced Delivery of AAV Vector in Parkinsonian Monkeys; In Vivo Detection of Gene Expression and Restoration of Dopaminergic Function Using Pro-Drug Approach". Experimental Neurology, vol. 164, pp. 2-14, 2000.

Barua, Neil U. et al. "Intrastriatal Convection-Enhanced Delivery Results in Widespread Perivascular Distribution in a Pre-Clinical Model". Fluids and Barriers of the CNS, vol. 9:2, pp. 1-12, 2012.

Bienemann A. et al. "The Development of an Implantable Catheter System for Chronic or Intermittent Convection-Enhanced Delivery." Journal of Neuroscience Methods, vol. 203, pp. 284-291, 2012.

Bobo, H. R. et al. "Convection-Enhanced Delivery of Macromolecules in the Brain". Proceedings of the National Academy of Sciences of the United States of America, vol. 91, pp. 2076-2080, 1994.

Chen, Michael Y. et al. "Variables Affecting Convection-Enhanced Delivery to the Striatum: A Systematic Examination of Rate of Infusion, Cannula Size, Infusate Concentration, and Tissue-Cannula Sealing Time". Journal of Neurosurgery, vol. 90, pp. 315-320, 1999.

Degen, Jeffrey W. et al. "Safety and Efficacy of Convection-Enhanced Delivery of Gemcitabine or Carboplatin in a Malignant Glioma Model in Rats." Journal of Neurosurgery , vol. 99, pp. 893-898, 2003.

Gill, Steven S. et al. "Direct Brain Infusion of Glial Cell Line-Derived Neurotrophic Factor in Parkinson Disease." Nature Medicine, vol. 9, No. 5, pp. 589-595, 2003.

Krauze, Michal T. et al. "Effects of the Perivascular Space on Convection-Enhanced Delivery of Liposomes in Primate Putamen". Experimental Neurology, vol. 196, pp. 104-111, 2005.

Krauze, Michal T. et al. "Reflux-Free Cannula for Convection-Enhanced High-Speed Delivery of Therapeutic Agents". Journal of Neurosurgery, vol. 103, pp. 923-929, 2005.

Lang, Anthony E. et al. "Randomized Controlled Trial of Intraputamenal Glial Cell Line-Derived Neurotrophic Factor Infusion in Parkinson Disease". Annals of Neurology, vol. 59, pp. 459-466, 2006.

Lidar, Zvi et al. Convection-Enhanced Delivery of Paclitaxel for the Treatment of Recurrent Malignant Glioma: A Phase I/II Clinical Study. Journal of Neurosurgery, vol. 100, pp. 472-479, 2004.

Richardson, Mark R. et al. "Interventional MRI-Guided Putaminal Delivery of AAV2-GDNF for a Planned Clinical Trial in Parkinson's Disease." Molecular Therapy, vol. 19, No. 6, pp. 1048-1057, 2011.

Sebastian, Waldy S. et al. "Safety and Tolerability of Magnetic Resonance Imaging-Guided Convection-Enhanced Delivery of AAV2-HAADC With a Novel Delivery Platform in Nonhuman Primate Striatum". Human Gene Therapy, vol. 23, pp. 210-217, 2012.

Sillay, Karl et al. "Benchmarking the ERG Valve Tip and MRI Interventions Smart Flow Neurocatheter Convection-Enhanced Delivery System's Performance in a Gel Model of the Brain: Employing Infusion Protocols Proposed for Gene Therapy for Parkinson's Disease". Journal of Neural Engineering, vol. 9: 026009, pp. 1-13, 2012.

(56) References Cited

OTHER PUBLICATIONS

Tanner, Phillip G. et al. "Effects of Drug Efflux on Convection-Enhanced Paclitaxel Delivery to Malignant Gliomas: Technical Note". Neurosurgery, vol. 61, No. 4, pp. 880-882, 2007.

White, Edward et al. "An Evaluation of the Relationships Between Catheter Design and Tissue Mechanics in Achieving High-Flow Convection-Enhanced Delivery". Journal of Neuroscience Methods, vol. 199, pp. 87-97, 2011.

White, E et al. "A Robust MRI-Compatible System to Facilitate Highly Accurate Stereotactic Administration of Therapeutic Agents to Targets Within the Brain of a Large Animal Model". Journal of Neuroscience Methods, vol. 105, pp. 78-87, 2010.

Yin, Dali et al. "Optimized Cannula Design and Placement for Convection-Enhanced Delivery in Rat Striatum". Journal of Neuroscience Methods, vol. 187, pp. 46-51, 2010.

Yin, Dali et al. "Cannula Placement for Effective Convection-Enhanced Delivery in the Nonhuman Primate Thalamus and Brainstem: Implications for Clinical Delivery of Therapeutics". Journal of Neurosurgery, vol. 113, pp. 240-248, 2010.

Dec. 21, 2012 Search Report issued in British Patent Application No. 1215092.6.

Oct. 3, 2013 International Search Report issued in International Patent Application No. PCT/GB2013/051973.

* cited by examiner

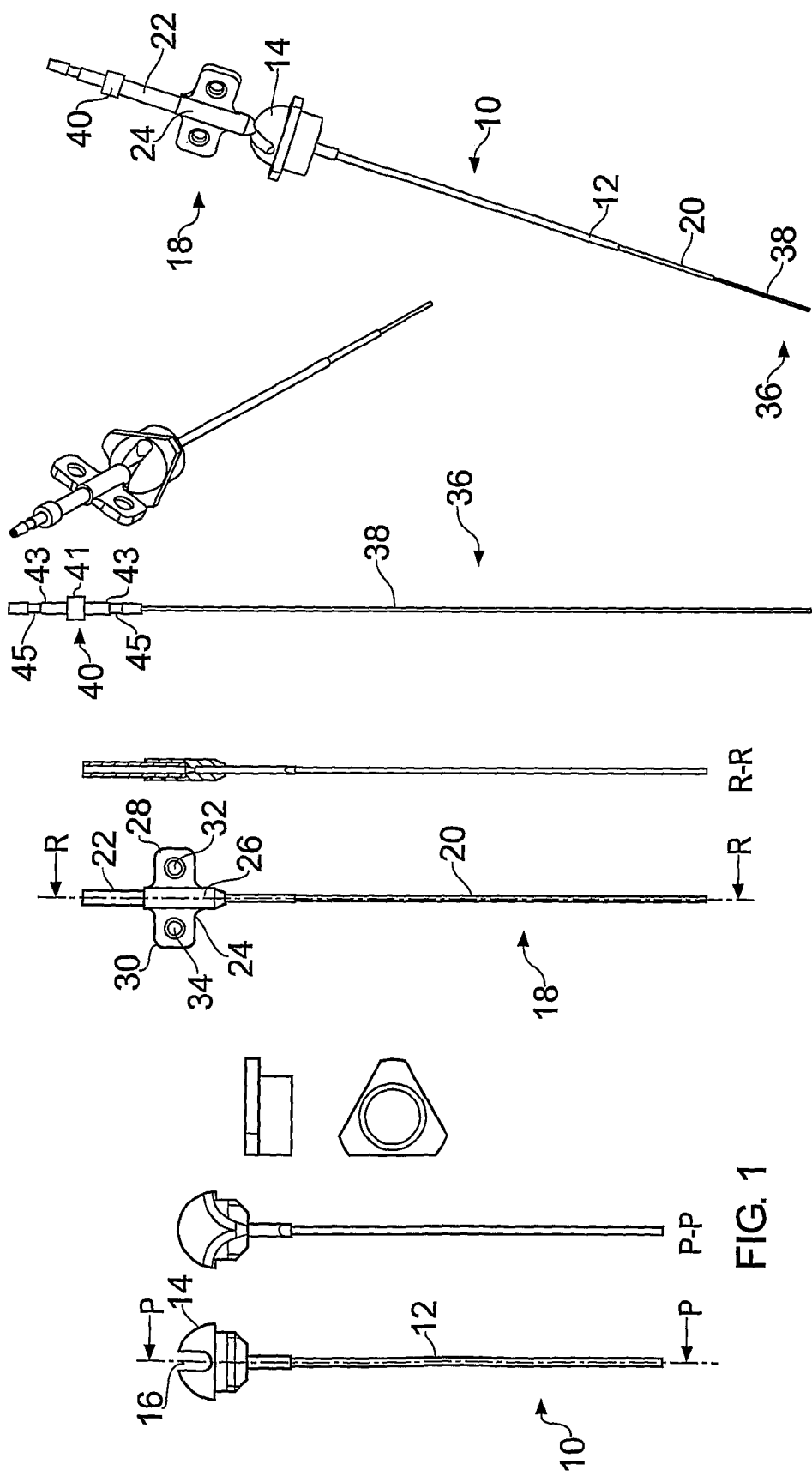

NEUROSURGICAL INSTRUMENTS

FIELD OF THE INVENTION

The present invention relates to apparatus for use in neurosurgery, in particular it relates to the design and use of catheters that are used to deliver therapeutic agents to the Central Nervous System.

The blood-brain barrier represents a considerable hurdle to the delivery of therapeutic agents to the nervous system. The term therapeutic agent includes substances which have a therapeutic effect, such as pharmaceutic compounds, genetic materials, biologics (i.e. preparations synthesised from living organisms such as stem cells). The development of techniques to bypass this barrier could revolutionise the management of Parkinson's, Huntingdon's and Alzheimer's disease as well as Glioblastoma Multiforme. Novel agents that could potentially suppress or even reverse the underlying pathological processes of these conditions have been developed. However, the limitations of these therapeutic agents lie in their inability to cross the blood-brain barrier and consequently their failure to reach the necessary structures within the brain when delivered by conventional methods (e.g. oral or intravenously).

Convection-enhanced delivery (CED) allows the delivery of a therapeutic agent directly to the central nervous system, without the requirement of the therapeutic agent crossing the blood brain barrier. CED utilises fine intracranial catheters and low infusion rates to impart drugs directly into the brain extracellular space. In contrast to direct intraparenchymal injection, encapsulated cells and biodegradable polymers, CED does not depend on diffusion. The use of a carefully designed cannula with a precisely controlled infusion rate leads to the development of a pressure gradient, along which a therapeutic agent passes directly into the extracellular space. Consequently, it is possible to achieve controlled, homogeneous distribution even for relatively large molecules, over large volumes of the brain and spinal cord.

DESCRIPTION OF THE RELATED ART

International patent application WO 03/077764 discloses the implantation of a catheter in a human or non-human brain for intraparenchymal drug delivery. A drug may thus be pumped intermittently or continuously through the catheter to the desired brain target. For long term drug delivery, a pump containing a reservoir may be implanted subcutaneously and the reservoir refilled as necessary percutaneously through a palpable port.

The paper 'Focal delivery during direct infusion to brain: role of flow rate, catheter diameter, and tissue mechanics' published in Am J Physical Regal Integr Comp Physical Vol 277, Issue 4, R1218-R1229, October 1999 describes factors that govern drug delivery by direct interstitial infusion.

This paper discloses that at low flow rates of fluid through an implanted catheter it can be assumed that all the infused solution is delivered to the target tissue. However, at high flow rates, the solution can flow back up the catheter shaft leaking to the surface and reducing delivery to the tissue.

At these high flow rates, the infusate creates pressure on the tissue surrounding the catheter and causes the tissue to move away from the surface of the catheter, thereby creating an annular space extending along a portion of the catheter length. If the annular space is sufficiently long, it can become an extended source of infusate and distort the spherical symmetry of the infusate distribution. In extreme cases, this annular space may extend to the brain surface, resulting in loss of infusate directly into the cerebrospinal fluid.

The principal limitation of CED is that the distribution of drugs through the extracellular space can be unpredictable. The key factors affecting drug distribution of therapeutic agent by CED are catheter design, infusion flow-rate, site of catheter placement, charge of therapeutic agent and non-specific therapeutic agent binding. Although there have been a number of clinical trials attempting to administer therapies or biologically active agents to patients with neurodegenerative diseases, using this technique, the available evidence suggests that the catheters being used are incompatible with successful CED.

One of the key elements in the unpredictability of the distribution of the drug is back flow of the infused agent along the catheter's insertion track. The paper 'Convection enhanced delivery of therapeutics for brain disease and its optimization' Neurosurg Focus 20 (3):E12, 2006 Jun. 28 discloses that such back flow can happen for one of two reasons. First, backflow can occur if the catheter has mechanically disrupted the tissue enough to allow a gap to form around its outer wall. In such cases, the infused agent simply back flows along the gap, thereby reducing the percentage of infusate reaching its intended target. This backflow could also lead to scalp necrosis or the development of antibodies.

Even when no gap has formed during catheter insertion or when the tissue has sealed against the outer wall, a second type of backflow can occur. During this intrinsic backflow, pressure associated with the infusion process pushes against the tissues and causes them to separate minutely from the catheter, until the shear forces in the tissue balance the pressure field and the retrograde axial flow stops.

The applicants aim to reduce the amount of backflow by using a catheter of small diameter as disclosed in WO 03/077785. Fused silica is a preferred material for the catheter due to its low viral binding properties. These properties are important as therapeutic agents may be viral based for example herpes simplex virus which could bind to a substrate such as a catheter causing inefficient delivery. However, it has been shown that only a small percentage of a viral infusion would bind to fused silica and hence this is a preferred material for delivery.

When fluid flows through the catheter under pressure, the catheter undergoes a vibration. A catheter made of stiff material such as fused silica has a high natural frequency. When fluid is surging through the catheter it undergoes high frequency, small amplitude vibration. This vibration of the catheter causes the gap between the catheter and its surrounding tissue to increase, thereby increasing backflow.

SUMMARY OF THE INVENTION

A first aspect of the present invention provides a catheter assembly for insertion into the brain, the assembly comprising a first length of tubing made of a first material, the first length of tubing being surrounded by a second material, the second material being more flexible than the first material and having a hardness of less than 50 Rockwell E.

In a preferred embodiment, the second material comprises a second length of tubing concentric with the first length of tubing. Alternatively, the second material may be part of the first length of tubing.

The assembly may comprise an additional length of tubing, the additional length of tubing being concentric with the first length of tubing, wherein an annular gap is created between the first length of tubing and the additional length of tubing.

The additional length of tubing may be made of a material which is more flexible than the first material.

The first length of tubing may extend further than the additional length of tubing.

A second aspect of the invention provides a catheter assembly for insertion into the brain, the assembly comprising inner and outer concentric length of tubing with an annular gap between them.

Preferably the inner and outer lengths of concentric tubing are both stiff. The outer length of catheter may have a module of elasticity of greater than 30 GPa.

The inner length of tubing may comprise fused silica. The outer tube may comprise fused silica. The outer tube may comprise stainless steel. The inner length of tubing has a polyimide coating.

BRIEF DESCRIPTION OF THE DRAWINGS

Embodiments of the invention will now be described by way of example with reference to the following drawings:

FIG. 1 illustrates a side view of a guide tube;

FIG. 2 illustrates a side view of an inner tube;

FIG. 3 illustrates a side view of a catheter;

FIG. 4A is a side view of the assembled guide tube, inner tube and catheter;

DETAILED DESCRIPTION OF THE PREFERRED EMBODIMENTS

Figure 4B:
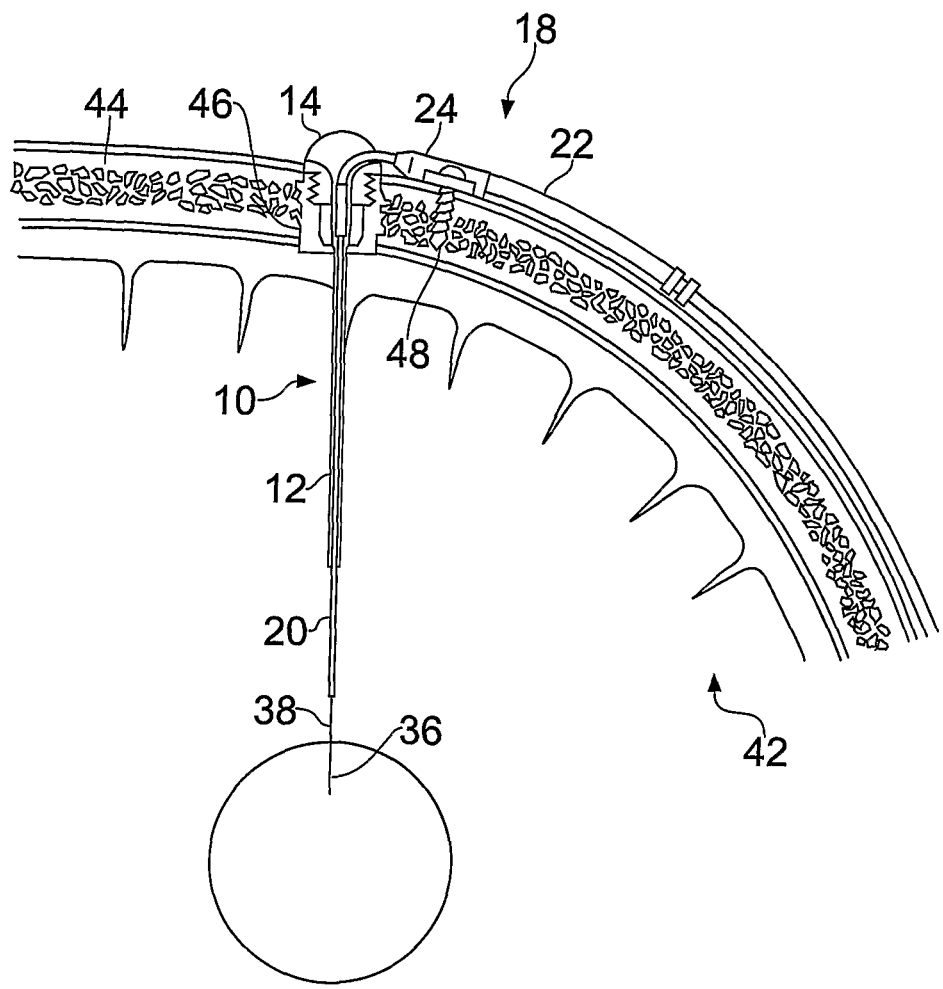
FIG. 4B illustrates the assembled guide tube, inner tube and catheter inserted into the brain.

FIGS. 1-3 illustrate a guide tube, inner tube and catheter respectively according to the present invention.

The guide tube 10 is shown in FIG. 1 and comprises a length of tube 12 with a hub 14 at one end. In this example it is made from a polyurethane plastic such as carbothane 55 DB20. However, it may be made from any material which is biocompatible and sufficiently rigid at room temperature to maintain its central aperture. In this example, the tube 12 has an outer diameter of 0.6 mm and an inner diameter of 0.5 mm.

The guide tube is inserted into the brain through an aperture (e.g. burr hole) in the skull created by the surgeon. Once the length of tubing is inserted into the brain, the hub can be attached to the patient's skull, for example by bonding into a burr hole in the skull using an acrylic cement. A wire may be used to guide the guide tube into place, as disclosed in WO03/07784. Before insertion, the guide tube is cut to a length short of the target. The distal end of the guide tube will typically fall several millimeters short of the target.

The hub of the guide tube is preferably domed and has a cut out slit 16 which links the central aperture of the tube to a side of the hub.

The inner tube 18 is illustrated in FIG. 2 and comprises two connected lengths of tubing, the distil tubing 20, which in this example has an outer diameter of 0.42 mm and an inner diameter of 0.2 mm and proximal tubing 22 which has a larger diameter. A stop element 24 links the proximal and distil tubing. The distal and proximal lengths of tubing are typically made of a polyurethane plastic, such as carbothane 85AB20, although other material could also be used. The stop element 24 is in this case also constructed using polyurethane plastic, such as carbothane 72 DB20. Again other suitable materials may be used.

The stop element 24 has a central body 26 which is generally cylindrical and a pair of diametrically opposed wings 28,30 each containing a countersunk hole 32,34 whereby the stop element may be screwed to the outer surface of the skull of the patient. The inner tube with distal and proximal lengths of tubing and stop element is described in more detail in WO03/077785.

The stop element has two roles. Firstly, when the inner tube is inserted into the guide tube, the stop element abuts against the hub of the guide tube, thereby forming a stop and defining the length of the distil tubing which extends from the tubing of the guide tube. Secondly, the wings of the stop element are used to fix the inner tube to the skull of the patient.

The role of fixing the inner tube to the skull of the patient may be accomplished by alternative means. For example, a pair of wings may be provided on the proximal tubing, for example by overmoulding onto the tubing. These wings may be provided with apertures to receive screws which when screwed into the skull fix the wings and proximal tubing in place. This arrangement allows one wing to be folded onto the other, so that a single screw is inserted through both apertures of the wings. This arrangement has the advantage that it causes some clamping of the catheter within the proximal tubing.

The catheter 36 is illustrated in FIG. 3 and comprises a fine length of tubing 38 and is typically made from fused silica. Alternative materials may be used which are inert and have low viral binding properties. The fused silica typically has an outer diameter of 0.2 mm and an inner diameter of 0.1 mm. The catheter is provided at one end with a barb 40 which acts as a stop. This may be directly moulded onto the catheter and may be made from a polyurethane plastic such as carbothane.

The barb 40 has a stepped cylindrical profile with a central aperture. A region of greatest diameter 41 has straight sides which form a stop against which the end of the proximal tubing abuts when the catheter is inserted into the inner tubing. On either side of the region of greatest diameter is a cylindrical portion 43 with a waisted 45 portion of decreased diameter. In use, tubing is pushed over the cylindrical portion until it abuts the region of greatest diameter 41. As the tubing passes over the waisted portion 45 it deforms to form a seal. As the catheter 36 is inserted into the inner tubing 18, the end of the proximal tubing 22 is pushed over one of the cylindrical portions 43. Connector tubing (not shown) which connects the catheter to a pump may be attached to the other cylindrical portion of the barb in the same manner.

In order to perform neurosurgery, the surgeon needs, in the first instance, to understand the patient's neuroanatomy and hence identify the position of the desired target. This is normally achieved by fixing a stereotactic reference frame to the patient's head, elements of which can be seen on diagnostic images, and from which measurements can be made. The stereotactic frame then acts as a platform from which an instrument is guided to a desired target using a stereoguide that is set to the measured co-ordinates. Once an instrument is guided to the desired target treatment can begin. This is described in more detail in WO03/077784.

The guide tube is inserted into the brain using the secured stereoguide and fixed in place as described above. FIGS. 4A and 4B illustrate the assembled guide tube 10, inner tubing 18 and catheter 36. FIG. 4A is the assembly outside the skull and FIG. 4B is the assembly with the catheter inserted into the brain 42. FIG. 4B illustrates the hub 14 of the guide tube 10 fixed in place in a hole in the skull 44 by bone cement 46. The inner tube is inserted into the guide tube by inserting the distil tubing 20 into the guide tube 10 until the stop element 24 abuts the hub 14 of the guide tube. The stop element 24 thus acts as a stop to control the amount the length of the inner tubing which is inserted into the brain. The catheter 36 is inserted into the inner tube and is pushed through until its barb abuts the end of the proximal tubing 22 of the inner tubing.

Once the guide tube, inner tube and catheter are all inserted, the proximal tubing containing the catheter extending out of the skull from the hub of the guide tube are bent through 90 degrees so that the stop element lies flat against the skull, as illustrated in FIG. 4B. This is then fixed in position using screws 48 passing through the countersunk holes. The cut out slit 16 in the hub 14 of the guide tube allows this 90 degree bend. Further clamping may be provided by additional fixing means on the inner tube (such as wings over moulded on the inner tube) through which screws may be attached to the skull.

The length of guide tube, inner tube and catheter are arranged so that the inner tube extends into the brain further than the guide tube (e.g. 10 mm) and the catheter extends into the brain further than the inner tube (e.g. 10 mm)

With the guide tube, inner tube and catheter all in place, the catheter can be connected to a pump (not shown) via connector tubing which connects to the barb of the catheter.

Figure 5:
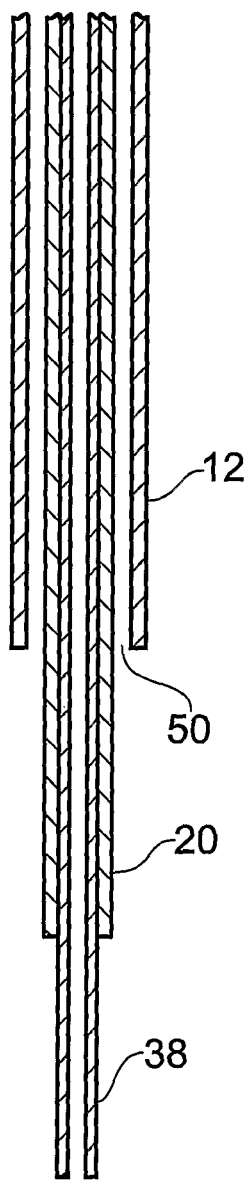
FIG. 5 is a cross section of the ends of the catheter, inner tube and guide tube inserted into the brain.

This arrangement has the advantage that it minimises vibration of the catheter this is described in more detail below with reference to FIG. 5, which shows an enlarged view of the end of the catheter, inner tubing and guide tube inserted into the brain.

When the guide tube is inserted into the brain it will fill with cerebro spinal fluid (CSF). The amount of cerebro spinal fluid in the guide tube will vary along its length. When inner tube and catheter are inserted into the guide tube, an annular gap 50 is created between the tubing 12 of the guide tube and the distil tubing 20 of the inner tubing and this annular gap will contain the cerebro spinal fluid. In this example the annular gap 50 is approximately 0.01 mm. As therapeutic agent is pumped to the end of the catheter and into the brain tissue, some backflow may occur along the outer surface of the catheter and inner tubing and some therapeutic agent in this backflow may pass by capillary action into the annular gap between the inner and outer tubing. The fluid between the inner tubing and guide tube has a damping action and reduces vibration of the catheter and inner tubing. Thus this arrangement of concentric tubing and an annular gap between the tubing creates a damping effect.

In this embodiment the catheter is made from a relatively stiff material, i.e. fused silica, whereas the inner tubing is made from a more flexible material (i.e. carbothane 85AB20). The use of a more flexible material in the inner tubing than the catheter also provides a damping effect, thus reducing or eliminating vibration of the inner and outer tubing.

In an alternative embodiment, the fused silica catheter could be over moulded with a more flexible substance, such as a polyurethane plastic to create the same effect.

The Thermedics Carbothane™ PC-3572D-B20 Polycarbonate based polythurane Biomedical Elaster has a hardness of 71 shore D. Materials with a stiffness of less than 50 Rockwell E provide sufficient damping.

Another suitable material is PEEK optima (manufactured by INVIBIO) which has a Rockwell (M) hardness of 99 (in its granular form).

The guide tube is also made of a more flexible material than the catheter (i.e. carbothane 85AB20) and this also contributes to the damping effect.

The inner tube is not essential to the invention and the catheter may be inserted directly into the guide tube. The flexible material of the guide tube and the annular gap between the guide tube and catheter both provide damping to the catheter.

The inner tube may be fabricated from a stiff material, for example having a modulus of elasticity of greater than 30 GPa. For example fused silica, which has a modulus of elasticity of 35-40 GPa or stainless steel suitable for surgical instruments or implant surgery which has a modulus of elasticity of 190-200 GPa. With a stiff inner tube, the damping is provided by the fluid in the annular gap between the catheter and the inner tubing. Alternatively, catheter may be inserted directly into a guide tube, without an inner tube, in which case the guide tube may be fabricated from a stiff material having the properties described above.

The invention claimed is:

1. A catheter assembly configured to be inserted into the brain, the assembly comprising:
    a guide tube comprising a hub configured to be attached to the skull and a length of tubing extending from the hub that is configured to be inserted into the brain; and
    a catheter comprising relatively stiff tubing partially surrounded by and bonded to a more flexible material, the catheter having an aperture at its distal end through which a therapeutic fluid can be delivered into the brain,
    wherein the catheter extends through the guide tube, from the hub to beyond a distal end of the length of tubing, such that the catheter is concentric with the length of tubing and an annular gap is provided between the catheter and the length of tubing,
    the annular gap extends to an opening in the distal end of the length of tubing and is configured to contain brain matter, and
    a part of the relatively stiff tubing not surrounded by and bonded to the more flexible material extends beyond the distal end of the length of tubing, the relatively stiff tubing having sufficient stiffness to maintain the part along a straight trajectory during insertion into the brain.

2. A catheter assembly according to claim 1, wherein the flexible material and the length of tubing have the same stiffness.

3. A catheter assembly according to claim 1, wherein the length of tubing has a modulus of elasticity of greater than 30 GPa.

4. A catheter assembly according to claim 1, wherein the relatively stiff tubing comprises fused silica.

5. A catheter assembly according to claim 1, wherein the length of tubing comprises fused silica.

6. A catheter assembly according to claim 1, wherein the length of tubing comprises stainless steel.

7. A catheter assembly according to claim 1, wherein the annular gap is configured to contain cerebro spinal fluid.

8. A method of delivering a drug to the brain of a subject, the method comprising:
    implanting a catheter according to claim 1 in the brain of the subject; and
    delivering a therapeutic agent therethrough using convection enhanced delivery.

9. A catheter assembly according to claim 1, wherein the relatively stiff tubing of the catheter is over-moulded with the more flexible material.

10. A catheter assembly kit configured to be inserted into the brain, the kit comprising:
   a catheter having an aperture at its distal end through which a therapeutic fluid can be delivered into the brain, the catheter comprising relatively stiff tubing partially surrounded by and bonded to a more flexible material; and
   a guide tube comprising a hub configured to be attached to the skull and a length of tubing extending from the hub that is configured to be inserted into the brain,
   wherein the catheter has dimensions that allow the catheter to be inserted into the guide tube, from the hub to beyond a distal end of the length of tubing,
   when assembled, an annular gap is formed between the catheter and the length of tubing of the guide tube, the annular gap extending to an opening in the distal end of the length of tubing and dimensioned such that, in use, the annular gap can receive brain matter through the opening, and
   a part of the relatively stiff tubing not surrounded by and bonded to the more flexible material extends beyond the distal end of the length of tubing, the relatively stiff tubing having sufficient stiffness to maintain the part along a straight trajectory during insertion into the brain.

11. A catheter assembly kit according to claim 10, wherein the length of tubing comprises fused silica.

12. A catheter assembly kit according to claim 10, wherein the length of tubing comprises stainless steel.

13. A catheter assembly kit according to claim 10, wherein the relatively stiff tubing comprises fused silica.

14. A method of delivering a drug to the brain of a subject, the method comprising:
   implanting a catheter according to claim 10 in the brain of the subject; and
   delivering a therapeutic agent therethrough using convection enhanced delivery.

15. A catheter assembly kit configured to be inserted into the brain, the catheter assembly kit comprising:
   a guide tube comprising a hub configured to be attached to the skull and a length of tubing extending from the hub that is configured to be inserted into the brain; and
   a catheter comprising relatively stiff material partially over-moulded with more flexible material and comprising an aperture at its distal end through which a fluid can be delivered into the brain,
   wherein the catheter and the guide tube are dimensioned such that the catheter can be inserted into the guide tube, from the hub to beyond a distal end of the length of tubing, and when inserted, an annular gap is formed between the catheter and the guide tube, the annular gap extending to an opening at the distal end of the length of tubing and dimensioned such that, in use, the annular gap can receive brain matter through the opening, and
   the relatively stiff material of the catheter that is not over-moulded with the more flexible material extends beyond the distal end of the length of tubing, the relatively stiff material having sufficient stiffness to maintain the relatively stiff material along a straight trajectory during insertion into the brain.

16. A catheter assembly kit according to claim 15, wherein the relatively stiff material is fused silica.

17. A catheter assembly kit according to claim 15, wherein the relatively flexible material is carbothane.

18. A catheter assembly kit according to claim 15, wherein the relatively stiff material of the catheter is arranged to extend, in use, into the brain further than the guide tube and flexible material.

19. A catheter assembly kit according to claim 15, wherein there is a step between the relatively stiff material and the flexible material of the catheter.

20. A method of delivering a drug to the brain of a subject, the method comprising:
   implanting a catheter according to claim 15 in the brain of the subject; and
   delivering a therapeutic agent therethrough using convection enhanced delivery.

21. A catheter assembly kit configured to be inserted into the brain, the catheter assembly kit comprising:
   a guide tube comprising a hub configured to be attached to the skull and a first length of tubing extending from the hub that is configured to be inserted into the brain; and
   a catheter assembly comprising a second length of tubing and a third length of tubing,
   the second length of tubing being separate from the third length of tubing and configured to be insertable into the third length of tubing to be a close fit therein and to extend beyond a distal end of the third length of tubing to form a stepped profile, and
   the second length of tubing comprising an aperture at a distal end through which a fluid can be delivered into the brain,
   wherein the catheter assembly and the guide tube are dimensioned such that the second and third lengths of tubing can be inserted into the guide tube, from the hub to a distal end of the first length of tubing, and
   at least a portion of the catheter assembly has a fit in the first length of tubing that is not as close as the close fit of the second length of tubing in the third length of tubing such that an annular gap is formed between a portion of the third length of tubing and the first length of tubing, the annular gap extending to an opening in the distal end of the first length of tubing and configured to receive brain matter through the opening.

22. A method of delivering a drug to the brain of a subject, the method comprising:
   implanting a catheter assembly according to claim 21 in the brain of the subject, and
   delivering a therapeutic agent therethrough using convection enhanced delivery.

23. A catheter assembly kit according to claim 21, further comprising a wire configured to guide the guide tube into place in the brain.

24. A catheter assembly kit according to claim 21, wherein the third length of tubing comprises a stop element configured to abut against the hub of the guide tube, when the third length of tubing is inserted into the guide tube, to define a length of the third length of tubing that can be inserted into the guide tube.

25. A catheter assembly kit according to claim 21, wherein the second length of tubing comprises a stop configured to abut the third length of tubing, when the second length of tubing is inserted in the third length of tubing, to define a length of the second length of tubing that can be inserted into the third length of tubing.

26. A catheter assembly kit according to claim 21, wherein the guide tube has a uniform outer diameter.

27. A catheter assembly kit according to claim 21, wherein a difference between the outer diameter of the second tube and the inner diameter of the third tube is less than a width of the annular gap.

28. A catheter assembly kit according to claim 21, wherein the third tube comprises a stop that abuts against the hub of the guide tube to define a position of the distal end of the third tube when inserted in the guide tube.

29. A catheter assembly kit according to claim 21, wherein the second tube comprises a waisted portion configured to engage a portion of the third tube when the second tube in inserted into the third tube to form a seal.

\* \* \* \* \*